(12) United States Patent
Phan (10) Patent No.: US 8,522,974 B2
(45) Date of Patent: Sep. 3, 2013

(54) SHARPS CONTAINER

(75) Inventor: Vu Phan, Piscataway, NJ (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 1341 days.

(21) Appl. No.: 10/986,820

(22) Filed: Nov. 15, 2004

(65) Prior Publication Data
US 2006/0102504 A1    May 18, 2006

(51) Int. Cl.
    *B65D 83/10*       (2006.01)

(52) U.S. Cl.
    USPC ............................... 206/366; 83/167; 83/944

(58) Field of Classification Search
    USPC ............... 206/363–366, 571, 438; 220/324, 220/326, 827, 829, 830, 833, 834, 323; 30/124, 30/125, 131, 135; 83/167, 944; 232/62
    See application file for complete search history.

(56) References Cited

U.S. PATENT DOCUMENTS

| | | | |
|---|---|---|---|
| 2,962,155 A * | 11/1960 | Rusciano ..................... 206/365 |
| 3,736,824 A * | 6/1973 | Dunnican et al. ............... 83/167 |
| 3,779,429 A * | 12/1973 | Porcelli ........................ 222/500 |
| 3,888,350 A * | 6/1975 | Horvath ........................ 206/531 |
| 3,914,865 A * | 10/1975 | Oakes ............................ 30/131 |
| 4,035,911 A * | 7/1977 | Nethercutt et al. ............. 30/131 |
| 4,489,859 A * | 12/1984 | vom Hofe et al. ............. 222/183 |
| 4,614,035 A * | 9/1986 | Andrews ......................... 30/124 |
| 4,867,309 A * | 9/1989 | Germain ....................... 206/366 |
| 4,922,597 A * | 5/1990 | Ikeda et al. ..................... 29/240 |
| 4,969,379 A * | 11/1990 | Taylor et al. .................... 83/167 |
| 5,080,251 A * | 1/1992 | Noack ........................... 206/366 |
| 5,417,659 A * | 5/1995 | Gaba ............................ 604/110 |
| 2004/0244202 A1 * | 12/2004 | Bull et al. ....................... 30/124 |
| 2007/0102312 A1 * | 5/2007 | Cha et al. ...................... 206/363 |
| 2007/0179443 A1 * | 8/2007 | Johnson aka Mindes .... 604/110 |

FOREIGN PATENT DOCUMENTS

| | | | |
|---|---|---|---|
| EP | 1656902 A1 * | 5/2006 | |
| WO | WO 03/000321 A1 | 1/2003 | |

* cited by examiner

*Primary Examiner* — J. Gregory Pickett
(74) *Attorney, Agent, or Firm* — Roylance, Abrams, Berdo & Goodman, L.L.P.

(57) ABSTRACT

A sharps container is disclosed. The sharps container utilizes a blocking member which does not interfere with a needle being inserted into the sharps container, and a latch mechanism which does not require a protruding tab. The latch mechanism requires at least a dual action to open the sharps container, and limits the movement required for opening the sharps container.

15 Claims, 7 Drawing Sheets

SHARPS CONTAINER

BACKGROUND OF THE INVENTION

1. Field of the Invention

The present invention relates to safety devices, and in particular to a sharps container for cutting and storing hypodermic needles from syringes and pen needles. The invention also relates to a method for storing the needles and to a process of manufacturing the sharps container.

2. Discussion of the Background

After a hypodermic needle has been used for an injection, it is desirable to remove and store the hypodermic needle in a safe container.

A sharps container which is known in the art comprises an inner box member and an outer housing member. The box and the housing each have an aperture which is dimensioned to receive the hypodermic needle. The box and the housing are hingedly connected to each other so that in an open position the apertures of the box and the housing overlap and the needle may be inserted through both of the apertures to project into the box. After the needle has been inserted into the apertures, the box and the housing are moved with respect to each other, for example in a scissor motion, so that the needle is clipped. After being clipped, the needle drops into the box for storage and subsequent disposal.

The box maybe urged into the open position by spring action, and retained in a closed position by latching the housing with the box. When the container is in the closed position, the apertures of the box and the housing do not overlap, and therefore, the sharps cannot escape the box. However, when the latch is released, the box and the housing move into the open position with respect to each other so that the aperture of the box coincide with aperture of the housing, and therefore, there may exist a situation where a needle is liable to escape from the box through the apertures. An example of such a circumstance is when the openings are positioned such that the force of gravity forces the needle toward the openings and possibly through the openings.

A known solution to the problem of keeping needles from falling out of the box when in the open position is to include a blocking member in the interior of the box. The blocking member includes a ball movable between a blocking position, where the ball blocks the apertures of the box, and an unblocking position, where the ball does not block the aperture of the box. In particular, the ball is movable within the internal housing from the blocking position to the unblocking position, such that the ball is retained in the blocking position. When a needle is inserted into the opening of the box, the ball is forced away from the opening by the action of the inserted needle. After the needle has been broken off and subsequently falls into the box, the ball is returned to the blocking position.

That is, in the known devices, the metal ball was designed to normally block the needle aperture, and to move away from the aperture only when a needle inserted into the aperture moves the ball bearing out of the way. After the needle has been broken off (i.e., clipped and falls into the box), the ball rolls back in front of the needle aperture.

A drawback of such a blocking arrangement is that in many cases the needles do not fall freely into the box after being clipped, but become wedged against the ball, hampering its motion. This renders the device unusable because additional needles cannot be inserted due to the jam.

Another drawback of the known blocking mechanism is that it is not well-suited for short needles because the needles need to be a certain minimum length to push the ball completely out of the way. That is, when a short needle is inserted through both apertures, the ball does not get pushed completely out of the way, and after being clipped, the needle is not allowed to fall into the box, instead becoming wedged against the ball and jamming the aperture of the box.

As described above, the box and the housing are retained in the closed position by latching the box with the housing so that in the closed position the apertures of the box and the housing do not overlap, thereby effectively blocking the opening of the box and preventing the needles from falling out. However, several drawbacks have been observed with known mechanisms for latching the box and the housing. For example, known latch mechanisms include a tab which protrudes from the device and has been known to easily break off, thereby rendering the device unusable.

Another example of known latching mechanisms employs a single tab to retain the box and the housing in a hinged positioned. A drawback of such an arrangement is that the device is prone to inadvertent activation (i.e., inadvertent opening). Yet another drawback of the known latch mechanisms is that the tab is designed to be moved freely whereby the permitted excessive movement of the tab (beyond the range of movement required for unlatching the box and the hosing) facilitates breakage of the tab during the normal operation of the device.

SUMMARY OF THE INVENTION

The present invention addresses the above-noted drawback of the known sharps containers by providing a sharps container, a process of manufacturing thereof, and a method of storing needles, where a blocking member does not interfere with a needle being inserted into the sharps container, where a latch mechanism does not require a protruding tab, where a latch mechanism requires at least a dual action to open the sharps container, and where a latch mechanism limits the movement required for opening the sharps container.

An embodiment of the invention provides a sharps container comprising a space which accommodates at least one needle therein and an opening dimensioned to receive at least one needle therethrough, to be accommodated in the space. The sharps container includes a blocking member which blocks the opening when the opening is positioned so that at least one needle accommodated in the space is urged towards the opening, and otherwise, does not block the opening.

Another embodiment of the invention provides a process of manufacturing a sharps container which comprises forming an enclosed space for accommodating at least one needle therein, the enclosed space having an opening. In particular, the process provides forming a blocking member which blocks the opening when the opening is positioned so that at least one needle accommodated in the space is urged toward the opening, and otherwise, does not block the opening.

Yet another embodiment of the invention provides a method of storing at least one needle in a container by placing the needle through an opening in the container and blocking the opening only when the opening is positioned so that at least one needle accommodated in the space inside the container is urged toward the opening, and otherwise, not blocking the opening.

A further embodiment of the invention provides a sharps container, and a process of manufacturing thereof, which has an internal housing for accommodating at least one needle therein, and an opening, dimensioned to receive at least one needle therethrough to be accommodated in the housing. The sharps container has an external housing, which functions as a breaking member, comprising an engaging mechanism and another opening dimensioned to receive the at least one needle therethrough. When the sharps container is in an open position, the openings of the interior and external housings overlap allowing a needle to be inserted through both opening into the internal housing. When the sharps container is urged into a closed position, a force is applied to the needle by the movement of the breaking member (i.e., the external housing) and the internal housing relative to each other which reduces the area of overlap of the opening, whereby the needle is broken off when in a closed position. The engaging mechanism comprises at least two engaging members securing the internal housing and the external housing when in the closed position, so that the open position is achieved by manipulating both of the engaging members.

A still further embodiment of the invention provides a method for storing needles in a sharps container, which requires a step of performing at least a dual action to produce an open position of the sharps container. A non-limiting example of such a method includes producing the open position by simultaneously manipulating at least two engaging members which secure the sharps container in a closed position.

A still further embodiment of the invention provides a sharps container, and a process of manufacturing thereof, where the contour of the exterior surface of the engaging mechanism is essentially parallel to a contour of an exterior surface of the internal housing when in the closed position. Thus, protrusions which may break off or cause inadvertent opening (as in known devices) are avoided.

A still further embodiment of the invention provides a sharps container having an internal housing for storing needles and an engaging member for maintaining the sharps container in a closed positions, and a process of manufacturing thereof. In particular, the engaging member comprises at least one lever constructed such that manipulation of the engaging member to facilitate an open position comprises urging a lever of the engaging member toward the internal housing, so that the manipulation of the engaging member is limited by, for example, a distance between the interior surface of the engaging member and an exterior surface of the internal housing.

The above-noted solutions maybe implemented together, or in any desired combination, in a sharps container, in a process of manufacturing thereof, and in a method for storing needles, according to the invention.

BRIEF DESCRIPTION OF THE DRAWINGS

These and other objects and novel features of the invention will be more readily appreciated from the following detailed description when read in conjunction with the accompanying drawings, in which

FIGS. 5a-5f illustrate in detail a needle-storage (interior) housing of a sharps container according to an embodiment of the invention. FIG. 5b is a sectional view along line I-I of FIG. 5a, FIG. 5e is a sectional view of FIG. 5C along line II-II.

Throughout the drawings, like reference characters refer to like structures.

DESCRIPTION OF THE EMBODIMENTS OF THE INVENTION

Figure 3:
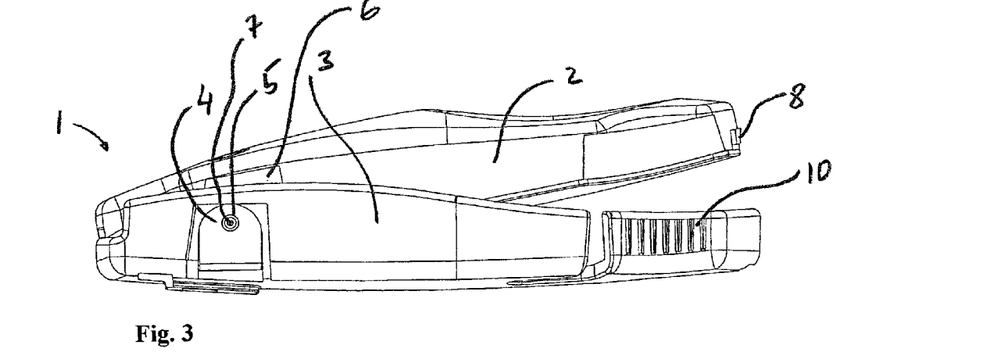
FIG. 3 is a side view of a sharps container in an open position according to an embodiment of the invention.
Figure 6:
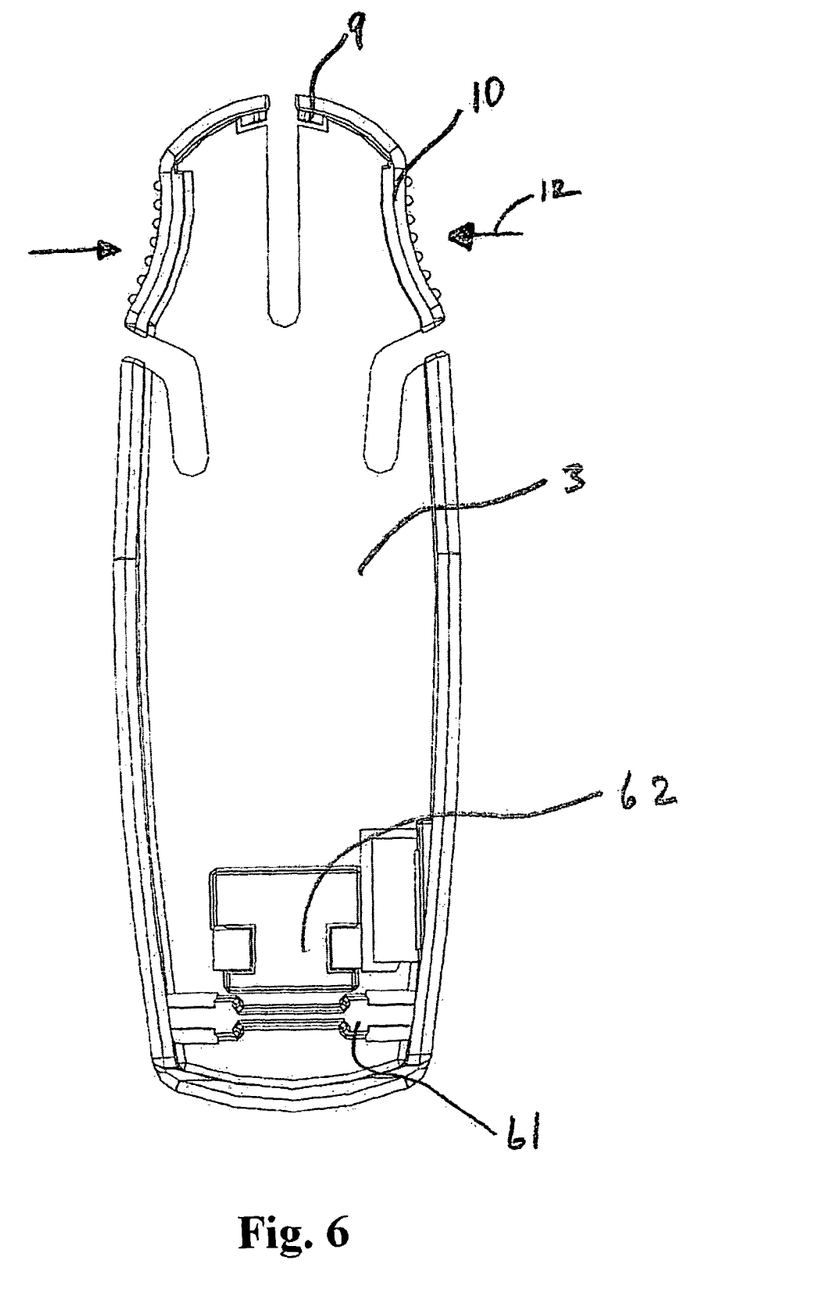
FIG. 6 is an illustration of a base (i.e., external housing which may serve as a breaking member) of a sharps container according to an embodiment of the invention.

Referring to FIGS. 1-4, a sharps container 1 comprises an internal housing (e.g., a box member) 2 which is pivotally mounted in an external housing (e.g., a breaking member) 3. The external housing 3 is provided with an external cutter 4 comprising a bent sheet of metal with an aperture 5 (see FIGS. 2 and 3). Internal housing 2 is provided with an internal cutter 6, comprising a metal disc with an internal aperture 7 (see FIGS. 3 and 4). When container 1 is in an open position, as illustrated in FIG. 3, apertures 5 and 7 overlap so as to permit insertion of a hypodermic needle, point first, into the box member 2. Container 1 is biased in the open position by, for example, a leaf spring 11 (shown in FIGS. 7c and 7d described below) formed from hardened spring steel. Container 1 can be moved into a closed position by pushing internal housing 2 into external housing 3 until tabs 8 engage with tabs 9 to retain the container in the closed position. A user can return container 1 to the open position by simultaneously pushing together, as shown, for example, in FIG. 6 (see arrows 11), levers 10 which have tabs 9 thereon to release the internal housing 2.

The internal housing 2 and external housing 3 are formed from, for example, 20% glass fiber filled polycarbonate. The external cutter 4 is formed from, for example, CS70 hardened and tempered steel, and the internal cutter 6 is formed from, for example, CS2 case hardened steel. Other non-limiting examples of materials which may be used for the external and internal cutters include, inter alia, 440A hardened stainless steel and/or PHI 17-7 precipitation hardened stainless steel.

Figure 4:
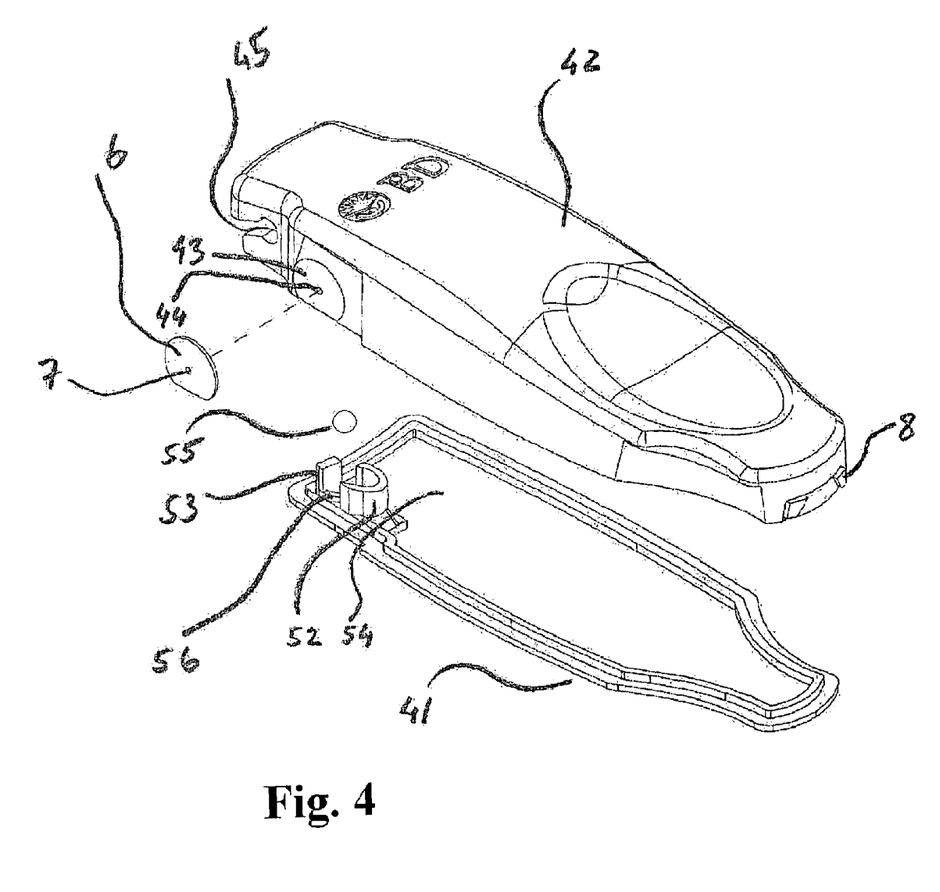
FIG. 4 is an illustration of a needle-storage (interior) housing of a sharps container according to an embodiment of the invention.

As shown in FIG. 4, the internal housing 2 comprises a base part 41 and a box part 42. The box part 42, which is, for example, ultrasonically welded to the base part 41, has a recess 43 in which an internal cutter is fit once the box part 42 and base part 41 are ultrasonically welded. An internal aperture 44 at the center of the recess 43 provides access for a needle to the inside of the internal housing 2. The box part 42 is provided with a molded groove 45 which snap-fits with the external housing 3 (see FIGS. 7c and 7d) to enable the assembled internal housing 2 to be pivotally mounted on the external housing 3.

Figures 5A, 5B:
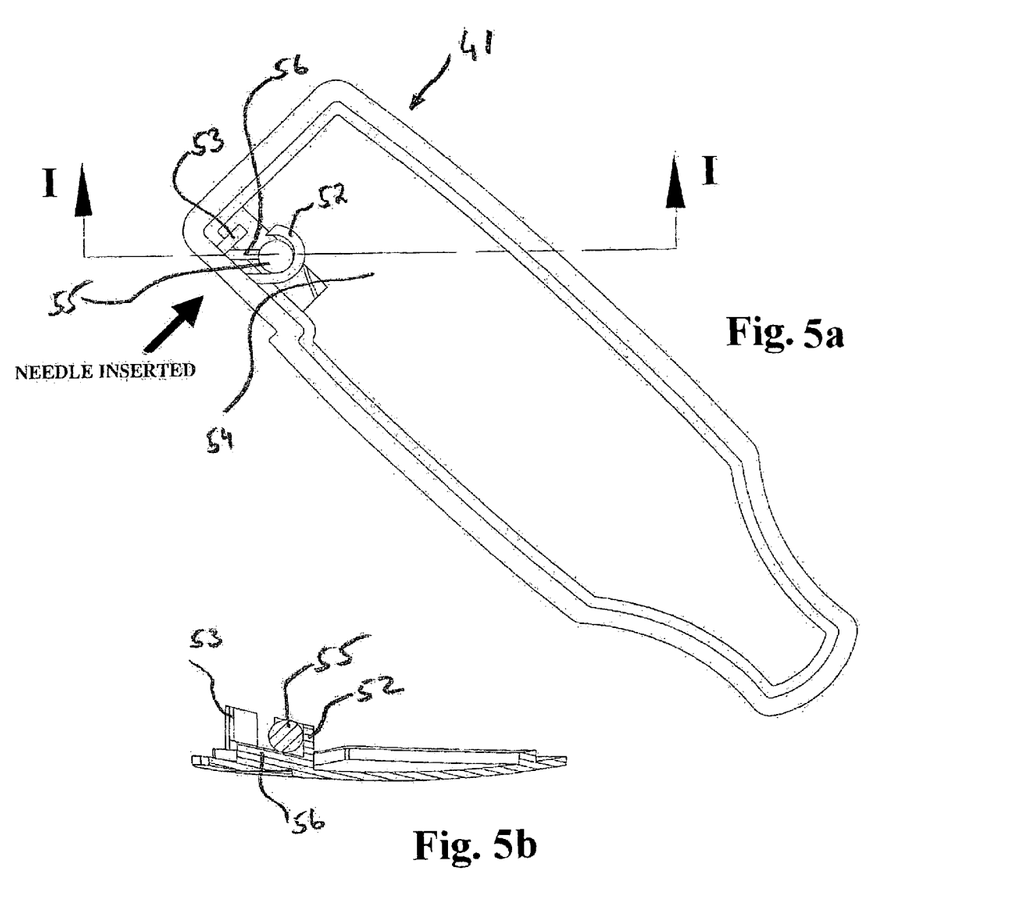
Figure 5C:
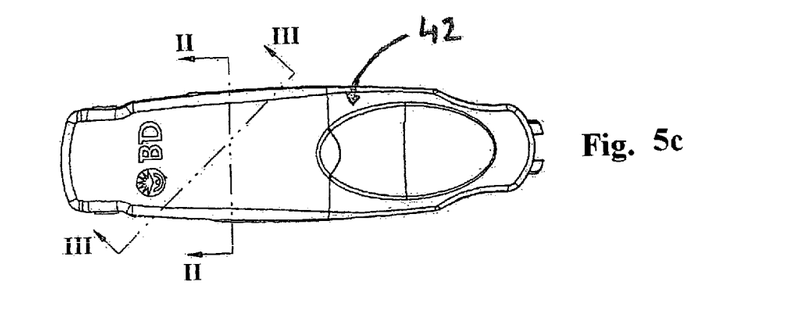
Figure 5D:
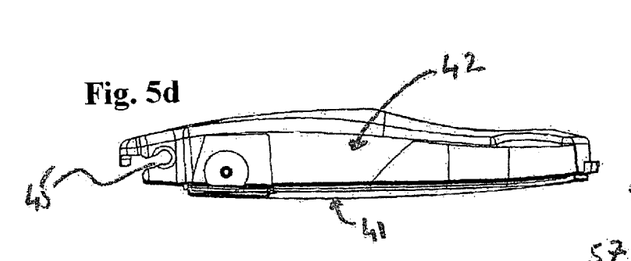
Figure 5E:
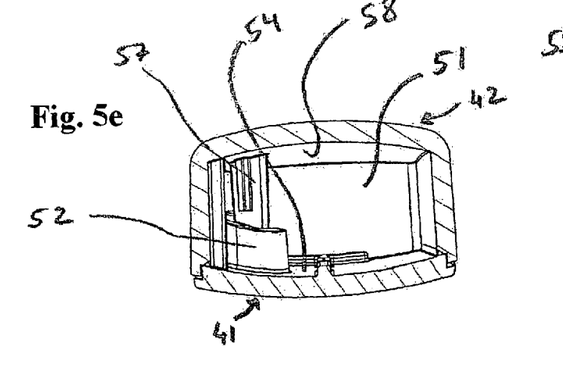
Figure 5F:
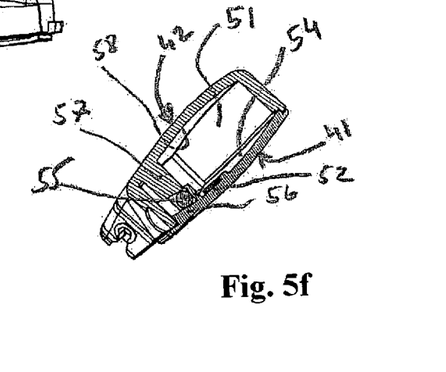
FIG. 5f is a sectional view of FIG. 5c along line III-III.

Referring to FIGS. 5a-5f, the inside 51 of the box part 42 is hollow for receiving and storing hypodermic needles (see FIGS. 5e and 5f). As shown in FIGS. 5a and 5b, base part 41 of internal housing 2 includes retaining walls 52 and 53 (see also FIG. 4) molded to internal surface 54 of the base part 41. The retaining walls 52 and 53 are constructed to retain a ball bearing 55 when the internal housing 2 is assembled by, for example, ultrasonic welding of the base part 41 to the box part 42. FIGS. 4 and 5a show a straight retaining wall 53 and a curved retaining wall 52. Retaining wall 52 is a single curved wall curved to retain the ball bearing 55; however, the single curved wall structure may be replaced by, for example, multiple retaining walls arranged with respect to each other to facilitate retention of ball bearing 55.

The base part 41 further comprises a ramp 56 molded to internal surface 54 of the base part 41 between the retaining walls 52 and 53. Ramp 56 has a downward slope towards the surface 54 in a direction away from the internal aperture 44. The design of ramp 56 facilitates ball bearing 55 blocking aperture 44 when container 1 is tilted in such a way that the needle apertures are at the lowest point of container 1.

The box part 42 comprises a rib 57 molded to its internal surface 58. Rib 57 is positioned such that when the internal housing 2 is assembled by, for example, ultrasonic welding of the base part 41 to the box part 42, rib 57 prevents ball bearing 55 from falling out of a guide channel formed by the retaining walls 52 and 53 (see FIGS. 5e and 5f). That is, when the base part 41 is welded to the box part 42, base part 41 and box part 42 cooperate to cage the ball bearing 55 (as shown, for example, in FIG. 5f).

As discussed above, a sharps contained 1 includes an internal housing 2 pivotally connected to an external housing 3. A shown in FIG. 6, the external housing 3 is provided with a pivot structure 61 for engagement with the groove 45 on the internal housing 2, and a retention structure 67 to retain a leaf spring 11.

Figure 7A:
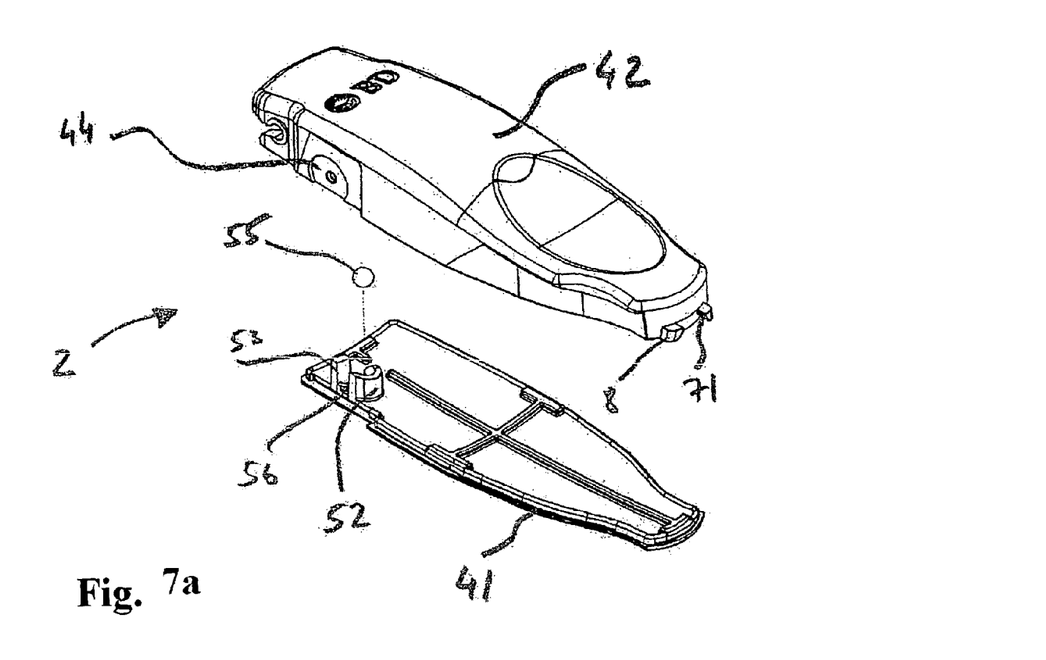
FIGS. 7a-7f illustrate a manufacturing process of a sharps container according to an embodiment of the invention.

External housing 3 comprises a transverse flex latch mechanism which allows one to easily open or close a sharps container. That is, as described above, the sharps container 1 has a stationary housing component (e.g., external member 3), which may be referred to as a base, and a needle storage component (e.g., internal member 2), which may be referred to as a lever, which is hinged to the base. The lever is permitted to move within a certain range of motion (see, for example, FIGS. 7e and 7f). Spring 11 is fixed to the base (3) and makes contact with the lever (2), thus urging it to one extreme of this range of motion. The transverse flex latch enables the user of the sharps container 1 to easily set the lever from one extreme to the other extreme. It accomplishes this by using two latch cams (e.g., tabs 8) on the lever and two latch cams (e.g., tabs 9) on the base. The two latch cams on the lever are a set distance apart. The two latch cams on the base are placed on flexible structures (e.g., levers 10), such that the distance between them may vary. As shown, for example, in FIGS. 7e and 7f, the two latch cam pairs (e.g., tabs 8 and 9, respectively) are arranged geometrically such that the latch cams on the base can interfere with the latch cams on the lever. In this mode, the latch cams on the base hold the lever in the closed position, against the spring which is urging the lever towards the open position. Squeezing the designated area on the device (see, for example, FIG. 6, arrows 12) causes the distance between the base latch cams to decrease and no longer be held back by the lever latch cams, which are a fixed distance apart. To close the device, the lever latch cams are forced past the base latch cams by means of angled surfaces (see, for example, surface 71 of tabs 8, as shown in FIG. 7a) which force the base latch cams together, allowing the lever latch cams to pass. Once they are clear, the base latch cams spring apart and constrain the movement of the lever (see, for example, FIG. 7f).

Figure 1:
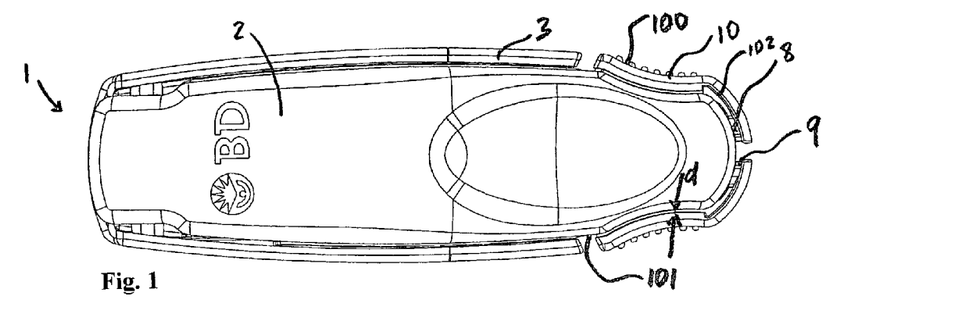
FIG. 1 is an overhead view of a sharps container according to an embodiment of the invention.
Figure 2:
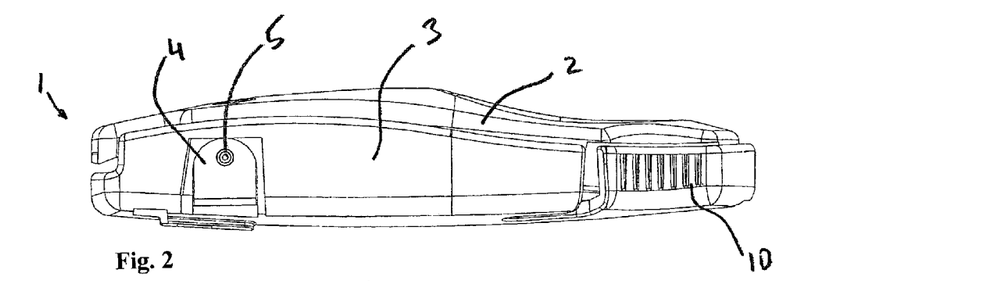
FIG. 2 is a side view of a sharps container in a closed position according to an embodiment of the invention.

As shown, for example, in FIG. 1, the contour of exterior surface 101 of external housing 3 is essentially parallel to the contour of the exterior surface 100 of the internal housing 2. That is, in contrast to previous devices, the transverse latch mechanism avoids having any protruding members (tabs or otherwise) on the exterior surface 101 of the external housing 3, even in the area of the latching mechanism. The latch cams which comprise tabs 8 and 9 are safely hidden away between the exterior surface 100 of the internal housing 2 and interior surface 102 of the external housing 3.

Furthermore, the movement of levers 10 to facilitate the opening of sharps container 1 is limited by the distance between the exterior surface 100 of the internal housing 2 and interior surface 102 of the external housing 3 (see, for example, FIG. 1, distance d).

Figure 7B:
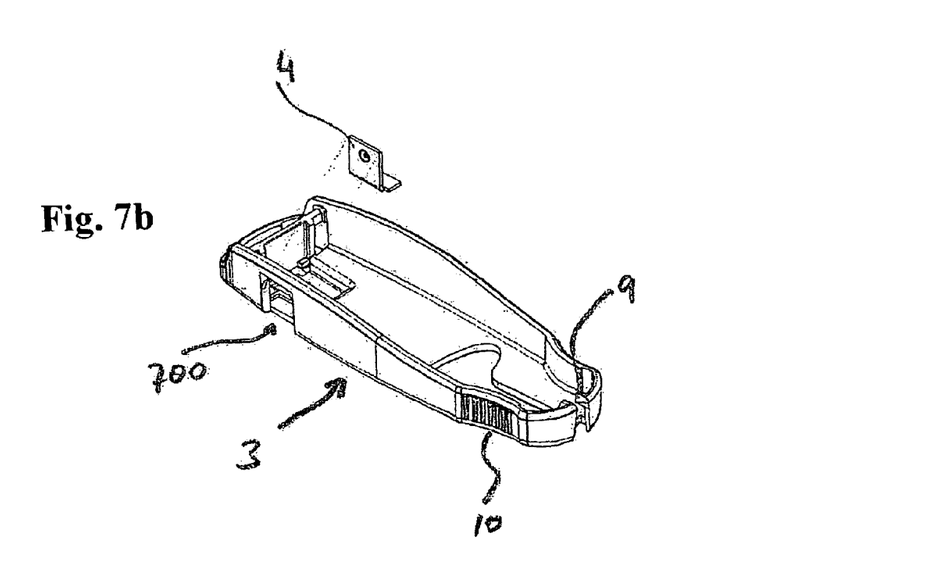
Figure 7C:
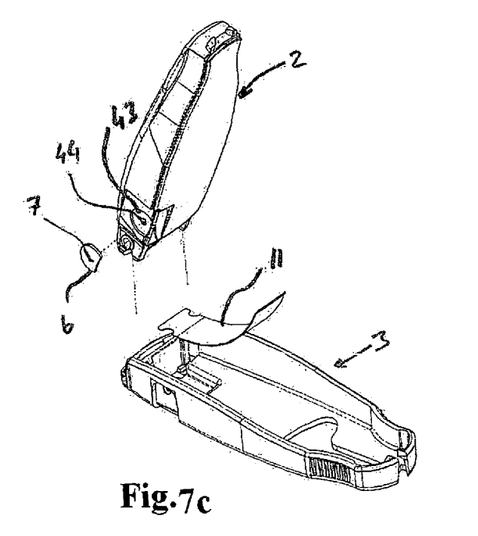
Figure 7D:
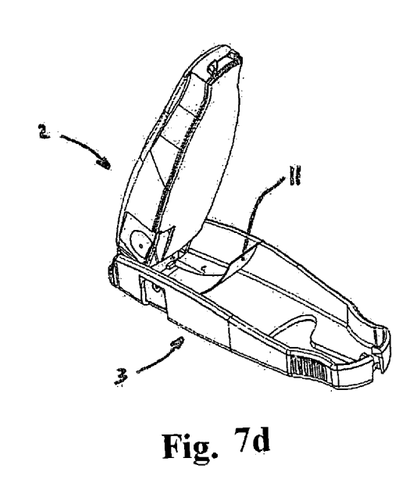

Referring to FIGS. 7a-7d, a process of manufacturing a sharps container according the invention comprises the following steps:

1. As shown in FIG. 7a, forming (preferably by injection molding) a base part 41 and a box part 42, where the base part 42 includes ball bearing retaining structure comprising walls 52 and 53 and a ramp 56, and the base part includes rib 57 (see FIG. 5e), and attaching base part 41 and box part 42 (preferably by ultrasonic welding) with ball bearing 55 placed in the retaining structure to complete the internal housing 2.
2. As shown in FIG. 7b, forming (preferably by injection molding) an external housing 3 comprising transverse latch mechanism structure (comprising levers 10 and tabs 9) and an opening 700 (for receiving an external cutter 4 comprising a bent sheet of metal with an aperture 5), and securing the external cutter 4 in the opening 700.
3. As shown in FIG. 7c, securing an internal cutter 6 in recess 43 of internal housing 2 making sure that openings 7 and 44 are aligned, and securing spring mechanism 11 to external housing 3.
4. As shown in FIG. 7d, hingedly attaching external housing 3 and internal housing 2.

Figure 7E:
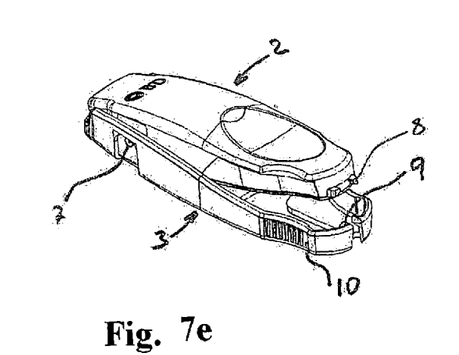
Figure 7F:
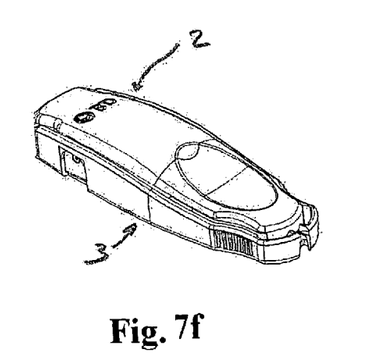

Referring to FIGS. 7e and 7f, during normal operation the natural position of the container 1 is such that, when a hypodermic needle (not shown) is pushed through the external aperture 5 and the internal aperture 7 when the container 1 is in the open position, the needle protrudes fully into the inside of the box part 42 of the internal housing 2 (FIG. 7e), and the ball bearing 55 is in an unblocking position due to the geometry of the ramp 56. When container 1 is urged into the closed position (FIG. 7f), the movement of the container 1 to the closed position cuts the needle (not shown) pushed through the external aperture 5 and the internal aperture 7 with a scissor movement and the needle drops into the box part 42 of the internal housing 2.

Due to the structure of the ball bearing guiding members including retaining walls 52, 53, ramp 56 and rib 57, only when the container 1 is held with apertures 5 and 7 nearest the ground, the ball bearing 55 rests over the internal opening 44, preventing egress of needles; otherwise, ball bearing 55 does not block opening 44.

While detailed descriptions of certain embodiments of the invention have been set forth above, a skilled artisan would readily appreciate that numerous additional modifications and variations of the present invention are possible in the light of the above teachings without departing from the spirit and scope of the invention. For example, internal housing 2 may further comprise a magnet which would facilitate retention of the needles within the box part 42, without adversely affecting the operation of the blocking mechanism which may include a ball bearing made of non-magnetic material (e.g., a ceramic). Thus, it is to be understood that the scope of the invention is set forth below in the appended claims and equivalents thereof.

I claim:
1. A sharps container comprising:
a first housing comprising a space, which accommodates at least one needle therein, and a first opening, dimensioned to receive at least one needle therethrough to be accommodated in the space; and a breaking member comprising an engaging mechanism and a second opening dimensioned to receive the at least one needle therethrough;

wherein the second opening and the first opening overlap when in an open position to receive the at least one needle through the first opening and the second opening via an area of overlap between the first opening and the second opening;

a force is applied to the needle by moving at least one of the breaking member and the first housing relative to each other to reducing the area of overlap, whereby the needle is broken off when in a closed position;

the engaging mechanism comprises:

a first engaging member securing the first housing and the breaking member when in the closed position; and a second engaging member securing the first housing and the breaking member when in the closed position; and the open position is achieved by manipulating the first engaging member and the second engaging member.

2. The sharps container as claimed in claim 1, wherein the first housing comprises at least one latch cam on an exterior surface the first engaging member comprises a first latch cam on the interior surface thereof;

the interior surface of the first engaging member facing the exterior surface of the first housing when in closed position;

the second engaging member comprises a second latch cam on the interior surface thereof, the interior surface of the second engaging member facing the exterior surface of the first housing when in closed position; and at least one of the first and the second latch cam engages the at least one latch cam on the exterior surface of the first housing when in the closed position.

3. The sharps container as claimed in claim 2, wherein the first housing comprises at least one other latch cam on the exterior surface thereof; and another of the at least one of the first and the second latch cam engages the at least one other latch cam on the exterior surface of the first housing when in the closed position.

4. The sharps container as claimed in claim 1, further comprising a spring mechanism which urges the breaking member with respect to the first housing in a direction facilitating the open position.

5. The sharps container as claimed in claim 1, wherein the open position is facilitated by essentially simultaneous manipulation of the first engaging member and the second engaging member.

6. The sharps container as claimed in claim 1, wherein the engaging mechanism comprises an exterior surface whose contour is essentially parallel to a contour of an exterior surface of the first housing when in the closed position.

7. The sharps container as claimed in claim 1, wherein the first engaging member comprises a first exterior surface whose contour is essentially parallel to a contour of an exterior surface of the first housing when in the closed position; and the second engaging member comprises a second exterior surface whose contour is essentially parallel to the contour of the exterior surface of the first housing when in the closed position.

8. The sharps container as claimed in claim 1, wherein the first engaging member comprises a first interior surface facing an exterior surface of the first housing;

the second engaging member comprises a second interior surface facing the exterior surface of the first housing; and the manipulating of at least one of the first engaging member and the second engaging member is limited, respectively, by a first distance between the first interior surface and the exterior surface of the first housing and by a second distance between the second interior surface and the exterior surface of the first housing.

9. A sharps container comprising:

a first housing comprising a space, which accommodates at least one needle therein, and a first opening dimensioned to receive at least one needle therethrough, to be accommodated in the space; and a breaking member comprising an engaging mechanism and a second opening dimensioned to receive the at least one needle therethrough;

wherein the second opening and the first opening overlap when in an open position to receive the at least one needle through the first opening and the second opening via an area of overlap between the first opening and the second opening;

a force is applied to the needle by moving at least one of the breaking member and the first housing relative to each other to reduce the area of overlap, whereby the needle is broken off when in a closed position;

the engaging mechanism secures the first housing and the breaking member when in the closed position; and the engaging mechanism comprises an exterior surface whose contour is essentially parallel to a contour of an exterior surface of the first housing when in the closed position.

10. The sharps container as claimed in claim 9, wherein the engaging mechanism comprises a first lever and a second lever; and the open position is facilitated by manipulating the first lever and the second lever.

11. The sharps container as claimed in claim 10, wherein the first housing comprises a first latch cam on an exterior surface thereof;

the engaging mechanism comprises a second latch cam on the interior surface thereof, the interior surface of the engaging mechanism facing the exterior surface of the first housing when in closed position;

the first latch cam engages the second latch cam when in the closed-position; and disengagement of the first latch cam and the second latch cam is facilitated by the manipulating of the first lever and the second lever.

12. The sharps container as claimed in claim 11, wherein the first housing further comprises a third latch cam on the exterior surface thereof;

the engaging mechanism comprises a fourth latch cam on the interior surface thereof;

the third latch cam engages the fourth latch cam when in the closed position;

the disengagement of the first latch cam and the second latch cam is facilitated by the manipulating of the first lever; and the disengagement of the third latch cam and the forth latch cam is facilitated by the manipulating of the second lever.

13. The sharps container as claimed in claim 9, further comprising a spring mechanism which urges the breaking member with respect to the first housing in a direction facilitating the open position.

14. The sharps container as claimed in claim 10, wherein the open position is facilitated by essentially simultaneous manipulation of the first lever and the second lever.

15. The sharps container as claimed in claim 10, wherein:
the first lever comprises a first exterior surface whose contour is essentially parallel to a contour of an exterior surface of the first housing when in the closed position;
and the second lever comprises a second exterior surface whose contour is essentially parallel to the contour of the exterior surface of the first housing when in the closed position.

\* \* \* \* \*